United States Patent
Abramovitch et al.

(10) Patent No.: US 6,579,247 B1
(45) Date of Patent: Jun. 17, 2003

(54) DEVICE FOR MONITORING BLADDER URINE DISTENSION IN PATIENTS, AND A METHOD THEREOF

(75) Inventors: Aharon Abramovitch, Givat Zeev (IL); Yuli Lozinski, Jerusalem (IL)

(73) Assignee: Alcor Medical Instruments, Inc., Wilmington, DE (US)

( * ) Notice: Subject to any disclaimer, the term of this patent is extended or adjusted under 35 U.S.C. 154(b) by 0 days.

(21) Appl. No.: 09/701,507

(22) PCT Filed: May 28, 1999

(86) PCT No.: PCT/IL99/00283

§ 371 (c)(1),
(2), (4) Date: Apr. 17, 2001

(87) PCT Pub. No.: WO99/62402

PCT Pub. Date: Dec. 9, 1999

(30) Foreign Application Priority Data

Jun. 1, 1998 (IL) ................................................. 124703

(51) Int. Cl.[7] .......................... A61B 5/103; A61B 5/00; A61B 5/02
(52) U.S. Cl. .................... 600/587; 600/438; 600/586
(58) Field of Search ................................. 600/552, 586, 600/561, 587, 438, 484; 29/235.5

(56) References Cited

U.S. PATENT DOCUMENTS

| | | | |
|---|---|---|---|
| 4,347,503 A | 8/1982 | Uyehara | |
| 4,738,260 A | 4/1988 | Brown | |
| 4,771,792 A | * | 9/1988 | Seale .......................... 600/552 |
| 4,926,871 A | 5/1990 | Ganguly et al. | |
| 4,977,906 A | 12/1990 | Di Scipio | |
| 5,022,402 A | * | 6/1991 | Schieberl et al. ........... 600/484 |
| 5,036,859 A | 8/1991 | Brown | |
| 5,058,591 A | 10/1991 | Companion et al. | |
| 5,239,997 A | * | 8/1993 | Guarino et al. ............. 600/587 |
| 5,853,005 A | * | 12/1998 | Scanlon ..................... 29/235.5 |

OTHER PUBLICATIONS

Preussner, P.R. "Kontinuierliche Registrierung des Fuellungszustandes der Menschlichen Harnblase" Biomedizinische Technik, vol. 36, No. 11, Nov. 1, 1991, pp. 285–287, XP000297137. (Abstract Only).

* cited by examiner

Primary Examiner—Marvin M. Lateef
Assistant Examiner—Ruby Jain
(74) Attorney, Agent, or Firm—Browdy and Neimark

(57) ABSTRACT

A device and method for monitoring condition of the patient's bladder urine distension level are presented. The device comprises a sensing unit and an indication unit. The sensing unit is attachable to a certain location on the patient's abdominal, and is of a kind transmitting acoustic signals substantially not exceeding 20 kHz to the urine bladder through tissue, receiving signals reflected from the urine bladder, and generating data representative of the condition of the bladder urine distention. A processor is interconnected between the sensing and the indication units. The processor is responsive to the generated data for analyzing the same and selectively generating a signal indicative of the existence of a predetermined condition of the patient's bladder urine distension level. The indication unit is responsive to the signal indicative of the existence of the predetermined condition for generating an indication signal aimed at attracting the attention of an authorized person, for example the patient himself.

22 Claims, 6 Drawing Sheets

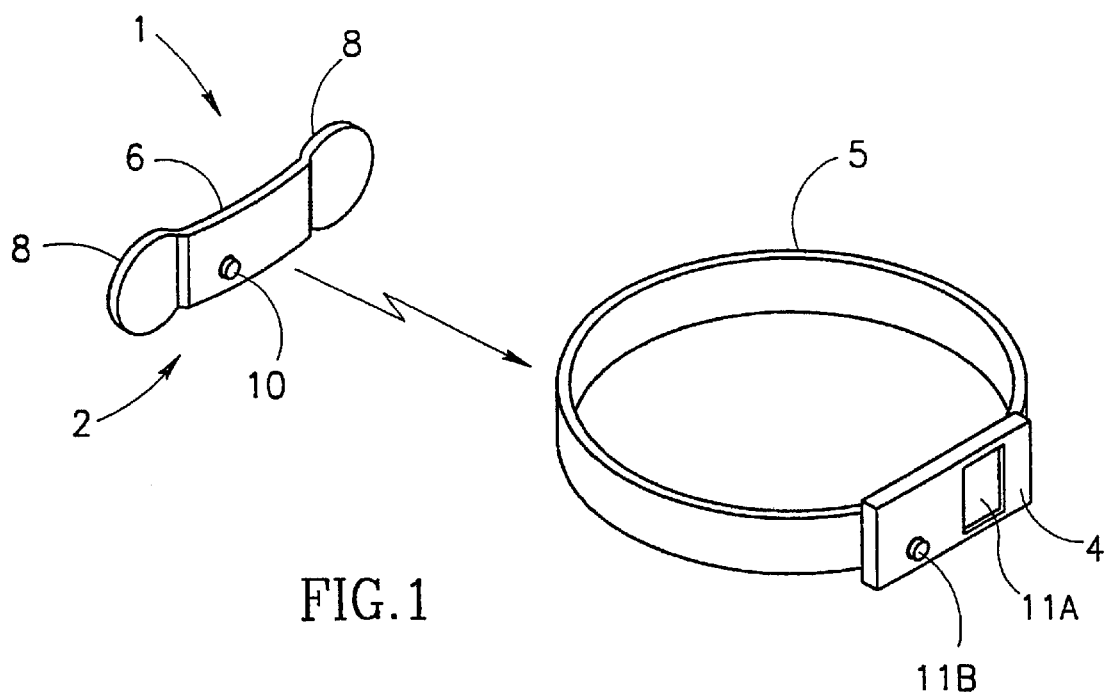
FIG.1
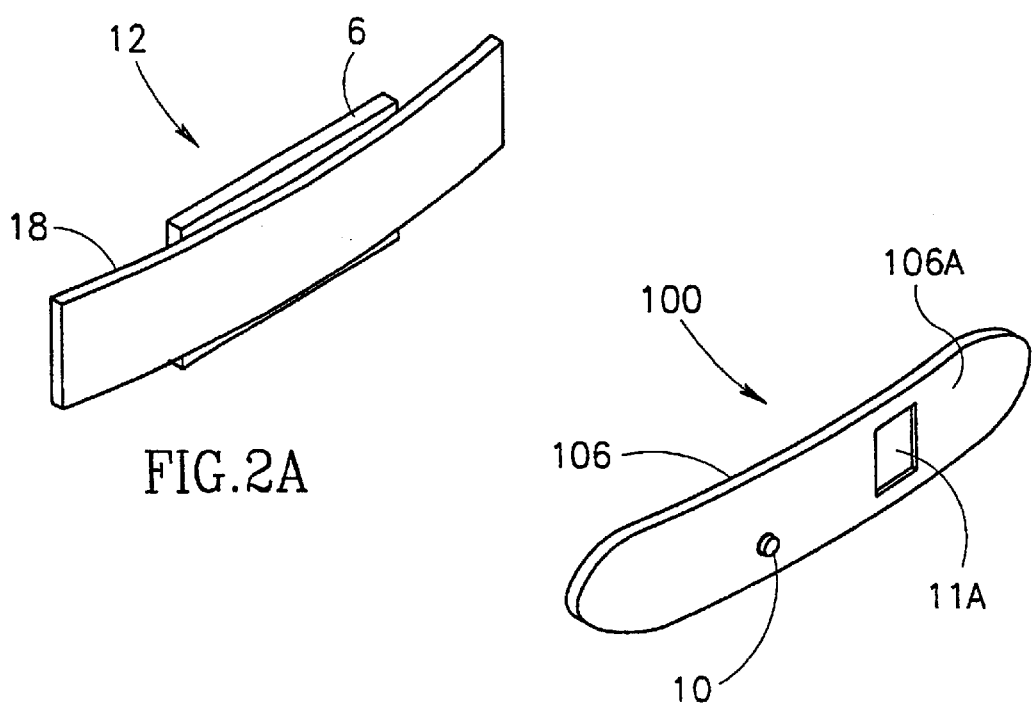
FIG.2A
FIG.2B

DEVICE FOR MONITORING BLADDER URINE DISTENSION IN PATIENTS, AND A METHOD THEREOF

The present application is the national stage under 35 U.S.C. 371 of PCT/IL99/00283, filed May 28, 1999.

FIELD OF THE INVENTION

This invention is in the field of monitoring techniques and relates to a method and device for monitoring the patient's bladder urine distention level, which is particularly useful in preventing of bedwetting.

BACKGROUND OF THE INVENTION

Bedwetting (involuntary enuresis) is a known problem, and various methods of treatment have been applied to patients suffering from this problem. According to statistical studies, bedwetting has an overall prevalence of up to 1% among the general population and up to 3% in late adolescence.

Various techniques aimed at solving this problem have been developed, and are disclosed, for example, in U.S. Pat. Nos. 4,347,503; 4,738,260; 4,977,906 and 5,036,859. All of them utilize a sensing pad for detecting the existence of initial drops of urine.

One of the most popular commercially available devices comprises a sensor of the type capable of detecting the existence of moisture, and an audio indicator coupled to the sensor through a wire. The patient attaches the device and puts it in operation just before going to bed. Upon detecting the initial drop(s) of urine, the sensor generates a signal which actuates the indicator to produce an alarm audio signal aimed at waking the patient.

U.S. Pat. Nos. 4,926,871 and 5,058,591 disclose techniques for the non-invasive automatic measurement of the volume of a human urine bladder. The technique disclosed in US '871 utilizes an ultrasonic transducer performing imaging of the urine bladder by means of transmitting a plurality of ultrasound signals into orthogonal planes. The technique disclosed in US '591 is based on the use of an ultrasonic transducer, which is attached to the patient's abdomen and performs a scanning of the urine bladder to obtain information indicative of its diameter, namely the space between the bladder's front and rear walls. The ultrasonic transducer is associated with a power source and is coupled to a suitable microprocessor. The microprocessor is preprogrammed for analyzing the information received from the transducer, and is capable of, upon detecting that the urine bladder's diameter has reached a predetermined, critical value, generating a signal indicative thereof. This signal is transmitted to a suitable alarm output circuit.

However, such an ultrasonic transducer, whose operational frequency is typically more that 20 kHz (as specifically indicated in US '591, the frequency of sound waves is 0.5 MHz), requires a voltage supply of up to 50V (12V, as indicated in this patent). This significantly increases the price of the entire device. Moreover, it is obvious, and specifically indicated in the patent, that the output of the receiver needs to be reduced to the range of 0–5V, thereby requiring an additional transformer, which both increases the price and complicates the construction of the device. Furthermore, it is understood that the power source supplying 12V has dimensions that do not allow miniaturization of the device, and its high price would not allow for making it a disposable device. It is clear from the illustrations in the patent that the dimensions of the sensor device are in the same order of those of the patient's urine bladder.

U.S. Pat. No. 5,239,997 discloses the use of low frequency sound waves for detecting abnormalities and quantification of defects in the portion of a human body. Here, the low frequency sound waves are applied such as to provide imitation of the effect of direct percussion on the body part to be examined.

SUMMARY OF THE INVENTION

There is accordingly a need in the art to facilitate the monitoring of bladder urine distention level to prevent bedwetting, by providing a novel device and method therefor.

It is a major feature of the present invention to provide such a device which is miniature, requiring a small amount of energy supply and easy to attach to the patient's body.

It is a further feature of the present invention to provide such a device which has a low cost and may therefore be disposable.

The main idea of the present invention is based on the following. To facilitate detecting the condition of the patient's urine bladder just prior to the need to urinate, there is actually no need for imaging the bladder itself. It is sufficient to collect signals reflected from the urine-containing bladder to estimate the current level (amount) of urine in the bladder. In other words, the complicated and expensive sensor-battery assembly used in the ultrasonic-based imaging technique can be replaced by a relatively inexpensive and portable assembly utilizing a sensor operating with acoustic waves in the frequency ranges of audio (16 Hz–20 kHz) or infrasound (less than 16 Hz) signals, which requires a relatively low power supply, as compared to that of the ultrasonic sensor. Consequently, such an inexpensive assembly may be disposable. If it is disposable, it may be designed like a piece of patch.

There is thus provided according to one aspect of the present invention, a device for monitoring the condition of bladder urine distention level of a patient, the device comprising:

(a) a sensing unit for attaching to a certain location on the patient's abdomen, the sensing unit being of the kind which transmits acoustic signals substantially not exceeding 20 kHz to the urine bladder through the patient's tissue, receives signals reflected from the urine bladder, and generates data representative of the condition of the bladder urine distention level;

(b) a processor responsive to said data for analyzing the data and selectively generating a signal indicative of the existence of the predetermined condition of the patient's bladder urine distention level; and (c) an indication unit responsive to said signal indicative of the existence of the predetermined condition for generating an indication signal to attract the attention of an authorized person.

According to another aspect of the present invention, there is provided a method for monitoring the condition of a patient's bladder urine distention level, the method comprising the steps of:

(i) attaching to a certain location of the patient's abdomen a sensing unit of the kind capable of transmitting acoustic signals substantially not exceeding 20 kHz to the urine bladder through tissue, receiving signals reflected from the urine bladder, and generating data representative of the condition of the bladder urine distention level;

(ii) actuating the sensing unit for transmitting said acoustic signals;

(iii) receiving and analyzing said data representative of the condition of the bladder urine distention level;

(iv) upon detecting that said data is indicative of the existence of a predetermined condition, generating an indication signal.

According to yet another embodiment of the invention, there is provided a device for monitoring the condition of bladder urine distention level of a patient, the device comprising:

a sensing assembly, a processor and an indication assembly accommodated in a substantially flat flexible case having one surface thereof coated with a gluing material for attaching the case to a certain location on the patient's abdomen, wherein the sensing assembly is of a kind capable of transmitting acoustic signals substantially not exceeding 20 kHz to the urine bladder through the patient's tissue, receiving signals reflected from the urine bladder and generating data representative of the condition of the bladder urine distention level, the processor is responsive to said data for analyzing the data and selectively generating a signal indicative of the existence of the predetermined condition of the patient's bladder urine distention level, and the indication assembly is responsive to said signal indicative of the existence of the predetermined condition for generating an indication signal to attract the attention of an authorized person.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 is a schematic illustration of a device for monitoring the condition of bladder urine distention level according to one embodiment of the invention;

FIG. 2A schematically illustrates a different example of a sensing unit suitable to be used in the device of FIG. 1;

FIG. 2B illustrates a device for monitoring the condition of bladder urine distention level according to another embodiment of the invention;

DETAILED DESCRIPTION OF A PREFERRED EMBODIMENT

Figure 3A:
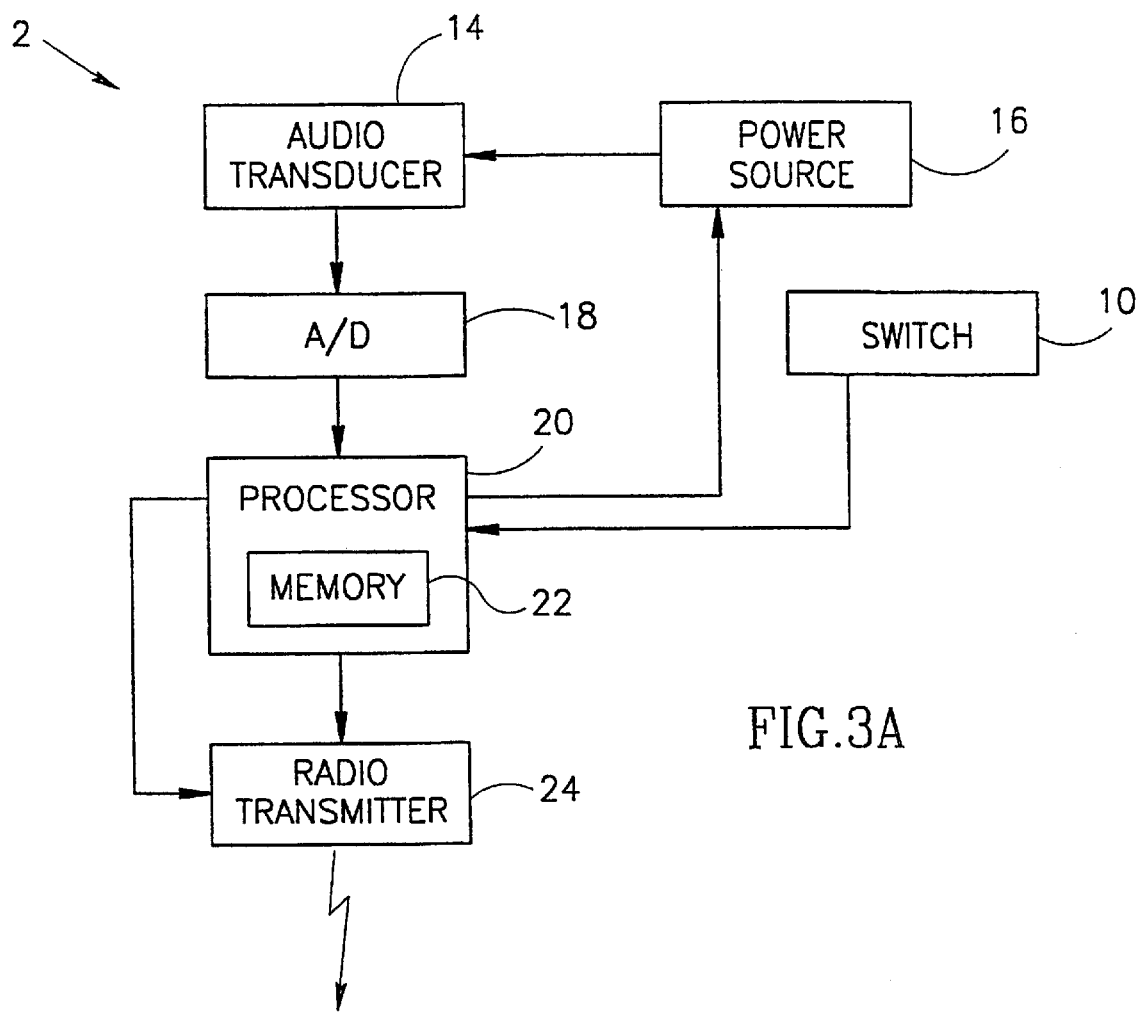
FIGS. 3a and 3b are block diagrams of the main components of, respectively, the sensing unit and an indication unit of the device of FIG. 1, constructed according to one embodiment of the invention.

Referring to FIG. 1, there is illustrated a device, generally designated 1, for monitoring the condition of a patient's bladder urine distention level. In the present example, the device 1 is a two-part device, one part being a sensing unit 2 and the other part being an indication unit 4.

The sensing unit 2 is designed in a manner to be attached to the patient's body at a location above his pubic bone. The sensing unit 2 is a miniature device shaped and dimensioned like a piece of patch. A central region 6 of the sensing unit 2 defines a sensing surface facing the patient's body, and a pair of end portions 8 are formed with a suitable gluing material to be adhered to the patient's body. The central region 6 is accommodated in an acoustically insulating case. A switching button 10 is provided on an outer surface of the sensing unit 2. The functional elements of the sensing unit will be described further below.

The indication unit 4 is supported on a strap 5, thereby presenting a wrist-mounted device. The indication unit 4 is attachable either to the patient's wrist or to that of an authorized person, e.g., the child's parent. It should be noted although not specifically shown, that such an indication unit 4 may be designed so as to be located in the vicinity of the patient or the authorized person, rather than being attached to his wrist. The unit 4 includes an indicator 11A, which may be either a loudspeaker providing an audio indication signal or a display providing a visual indication, and a switching button 11B for switching off the transmission of the indication signal. The functional elements of the indication unit will be described further below. The units 2 and 4 are wireless connectable to each other, i.e., through signaling.

FIG. 2a illustrates a further example of the design of the sensing unit suitable to be used in the device 1. A sensing unit 12, in distinction to the unit 2, has only that part 6 defining the sensing surface. As for the attachment means, a conventional patch 18 may be used to cover the part 6 and, whilst being glued, fix its location on the body.

Referring to FIG. 2b, there is illustrated a device 100 for monitoring the condition of the patient's bladder urine distention level, constructed according to another embodiment of the invention. In distinction to the above-described device 1, the device 100 is a one-part device shaped and dimensioned like a piece of patch. In other words, both the sensing and the indication units are incorporated into a common patch-like, acoustically insulating case 106. The switching button 10 and indicator 11A are located on one side 106A of the case 106, while the other side thereof facing the patient's body is at least partly coated with a gluing material to be adhered to the patient's body.

Figure 3B:
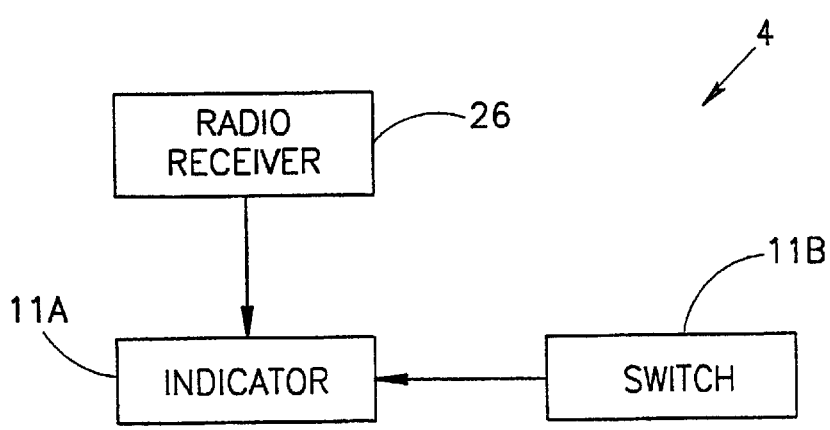

Reference is made to FIGS. 3a and 3b, illustrating the functional elements of, respectively, the sensing unit 2 and the indication unit 4 of the device 1. The sensing unit 2 includes a transducer 14 coupled to a battery power source 16. The transducer 14 is of a type generating pulses of audio (16 Hz–20 kHz) or infrasound (less than 16 Hz) signals. A piezoelectric element, for example made of a ceramic material, may be used as the transducer 14. It should be noted although not specifically shown, that the transducer 14 comprises a transmitter and one or more receiver. The purpose of using more than one receiver will be described more specifically further below. The battery power source 16 is of a small size, supplying an alternating voltage, practically not exceeding 5V, to the transducer 14. A conventional analog to digital (A/D) converter 18 is coupled to the transducer 14. It should, however, be noted that such a converter could be a constructional part of the transducer 14.

Coupled to the converter 18 (or to the transducer 14 including A/D means) is a processor 20, which is typically a chip with an embedded application. The processor 20 has a memory 22 for storing reference data, and is preprogrammed for analyzing signals coming from the transducer 14 with respect to the reference data, and for selectively generating a warning signal to be transmitted to the indication unit 4. In the example of FIG. 1, the sensing unit 2 and the indication unit 4 are wireless connected to each other. To this end, the sensing unit 2 is provided with a suitable transmitter 24 for generating and transmitting wireless transmittable signals, e.g., radio signals, while the indication unit 4 comprises a receiver 26 of a corresponding type for receiving these wireless transmittable signals.

To enhance the sensitivity of the monitoring device, the transducer 14 may comprise more than one receiver associated with a common transmitter. For example, the sensing unit may be dimensioned so as to extend along the entire urine bladder. In this case, either two receivers are located symmetrically with respect to the transmitter, or an array of spaced-apart receivers is used. The use of more than one receiver enables to determine the difference between signals detected by receivers at different locations relative to the urine bladder.

It should be noted that the processor 20 is a so-called "expert system" containing signal processing and computational intelligence for decision making. Such an expert system utilizes a logic utility based on decision tables and a learning mode of operation for periodically updating the reference data and, accordingly, decision tables, in view of the analysis results.

Figure 4A:
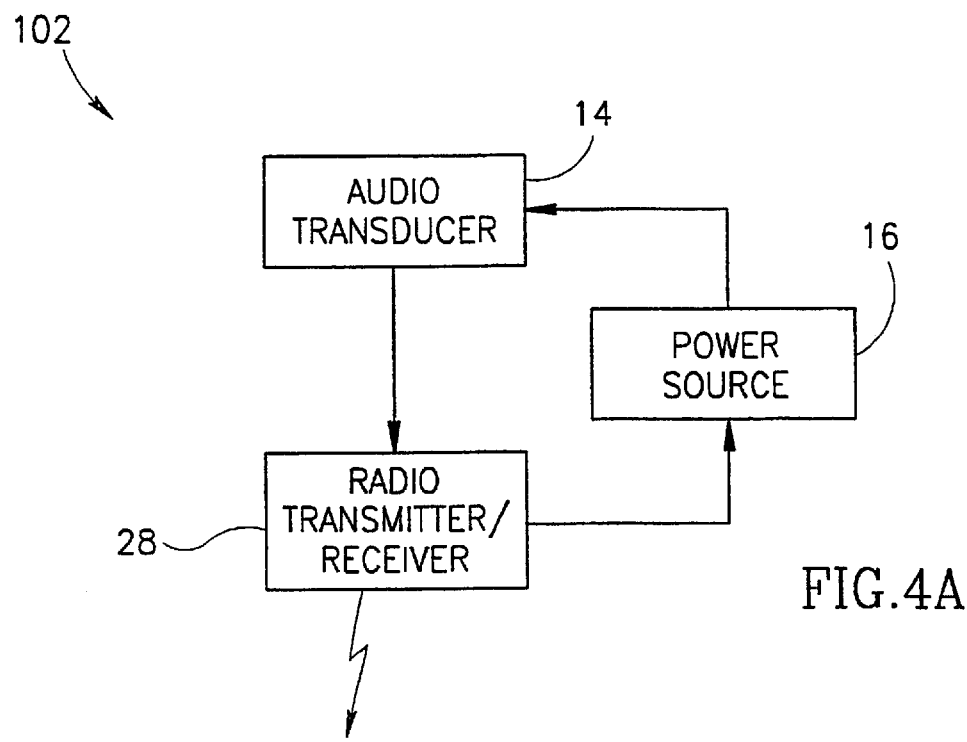
FIGS. 4a and 4b are block diagrams of the main components of, respectively, the sensing unit and an indication unit of the device of FIG. 1, constructed according to another embodiment of the invention.
Figure 4B:
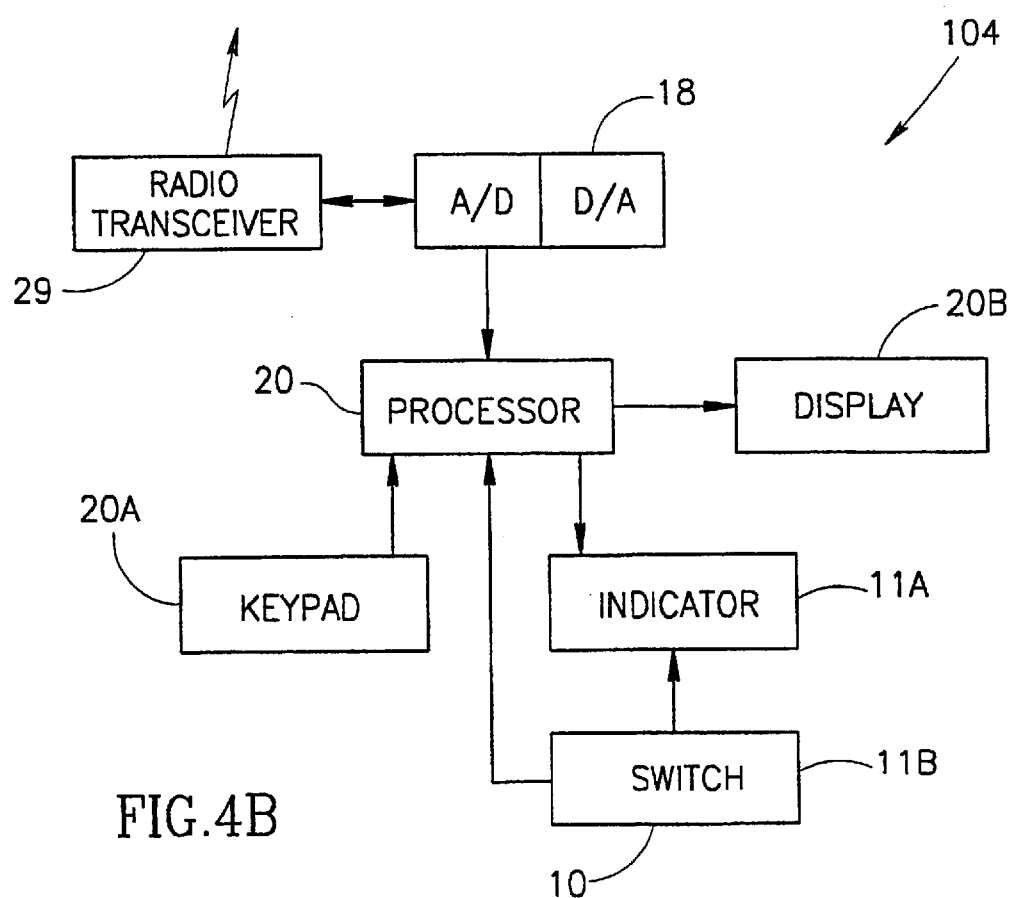

Turning now to FIGS. 4a and 4b, the functional elements of, respectively, sensing unit 102 and indication unit 104 have somewhat different constructions as compared to those of FIGS. 3a and 3b. Same reference numbers are used for identifying those components which are identical in the embodiments of FIGS. 3a–3b and 4a–4b. In this example, in distinction to that of FIGS. 3a–3b, the processor is a part of the indication unit 104, and both the sensing and indication units are provided with receiver/transmitters 28 and 29 for operating with wireless transmittable signals, e.g., radio signals. In other words, the entire monitoring device is operated from the indication unit 104. To this end, an analog to digital (A/D) and digital to analog (D/A) converter 18 is provided, being interconnected between the radio transceiver 29 and the processor 20.

The indication unit 104 is optionally equipped with a keypad 20a (constituting input means) and a display 20b, both coupled to the processor 20. A physician or other authorized person may thus enter the reference data associated with the specific patient into the memory of the processor, prior to delivering the device to the patient. For this purpose, a suitable interface including all necessary keys (menu) is presented on the display 20B.

Figure 5:
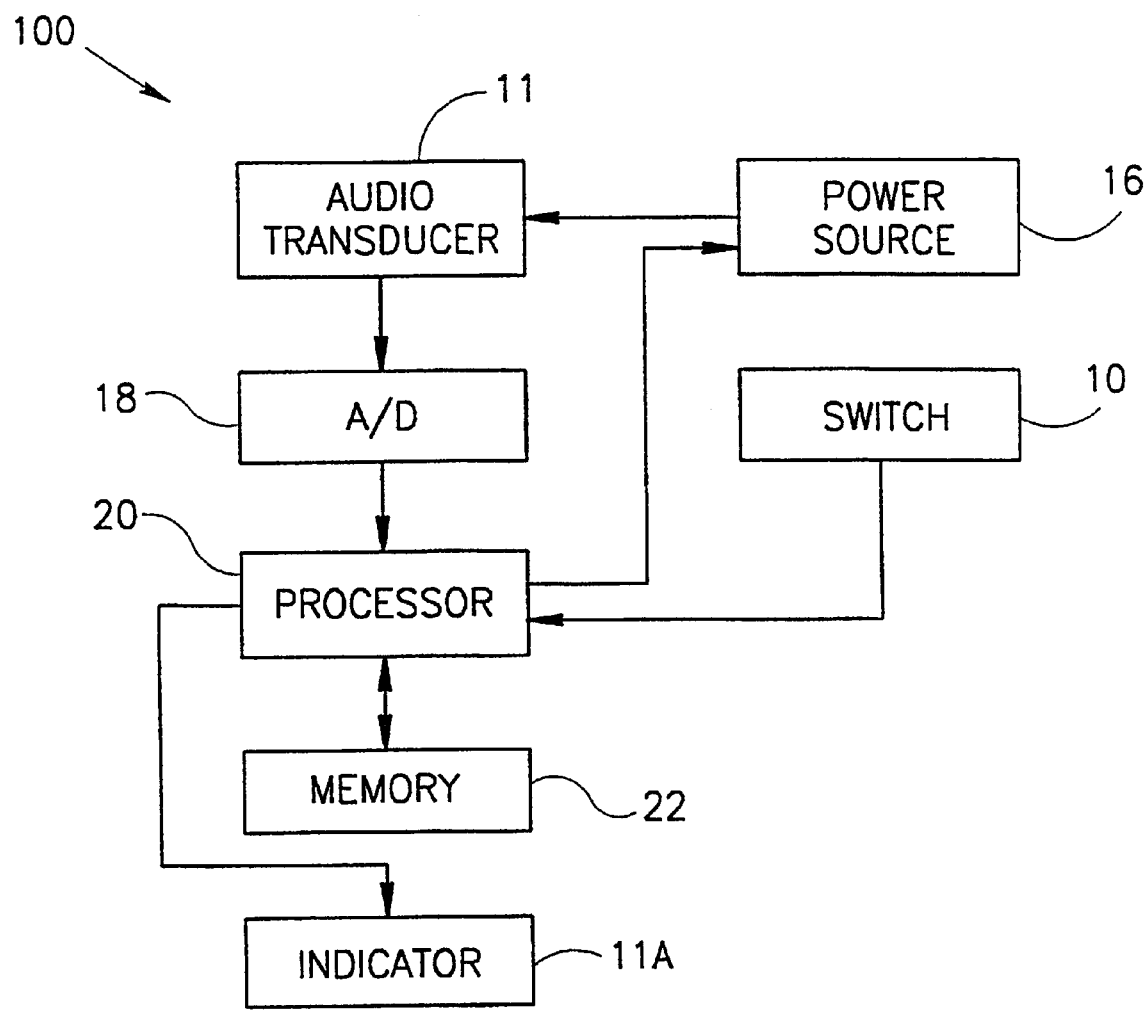
FIG. 5 is a block diagram illustrating the main components of the device of FIG. 2B.

Referring to FIG. 5, there are illustrated functional elements of the device 100 (FIG. 2b), using the same reference numbers for identifying common components with the previously described embodiments. Here, the processor 20 is directly connected to the indicator 11A. The indicator 11A, when being actuated by the processor 20, generates the indication alarm signal, which may be either visual or audio. Thus, the device 100 does not need any radio or the like transceiver.

Figure 6:
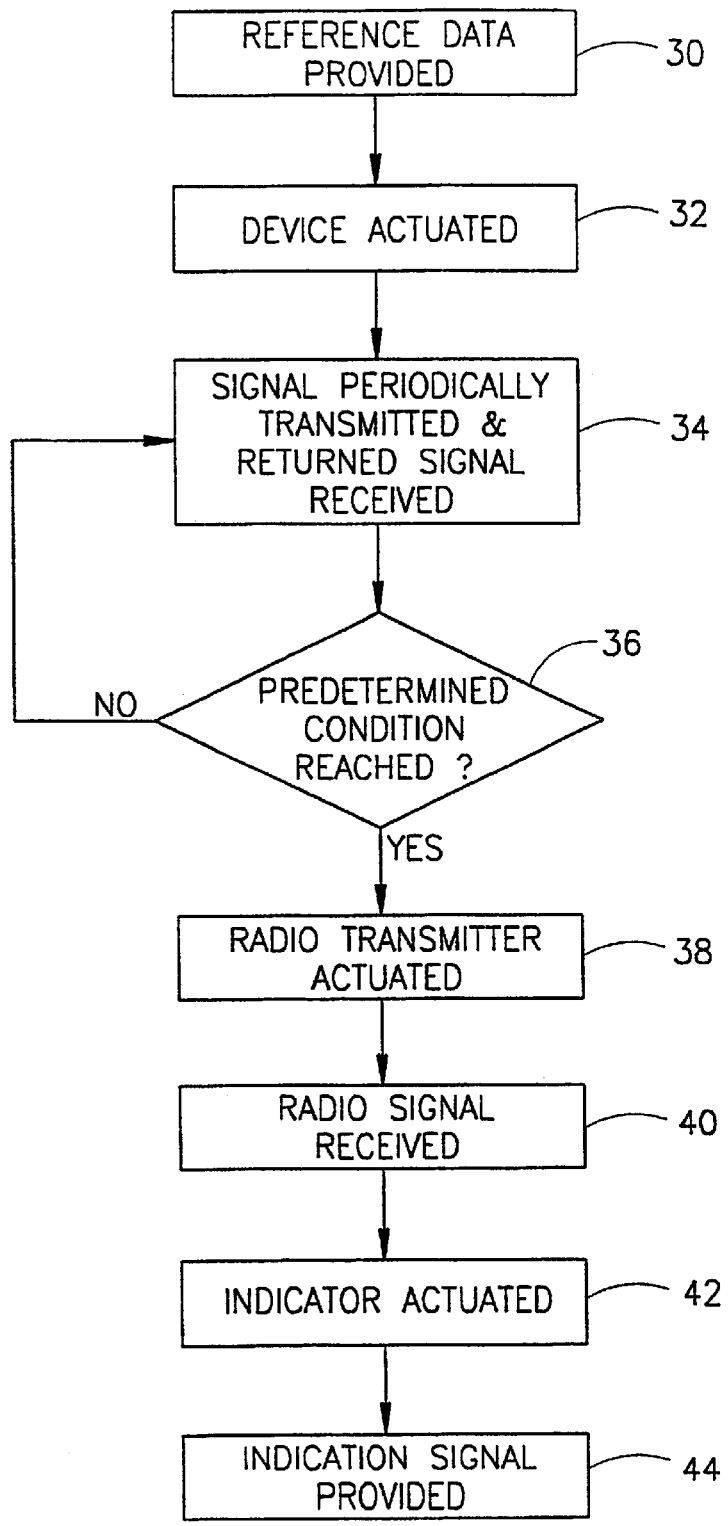
FIG. 6 illustrates a flow diagram of the main operational steps of the device according to the embodiment of FIGS. 3a–3b.

The operation of the device 1 constructed as exemplified in FIGS. 3a and 3b will now be described with reference to FIG. 6. The processor 20 is pre-set with the reference data stored in the memory 22 (step 30). This reference data is representative of peculiarities of the specific patient, namely a threshold value of the level (amount) of urine in the bladder corresponding to a condition wherein urination is about to occur (constituting a predetermined condition). The patient or an authorized person, as the case may be, attaches the sensing unit 2 to the patient's body at a location slightly above his pubic bone, attaches the indication unit 4 to the wrist, and puts the device in operation by pressing the switch button 10 (step 32). Pulses of audio or infrasound signals are periodically generated and transmitted by the transducer 14, for example every minute, and signals returned (reflected) from the urine in the bladder are detected (step 34). These detected signals are converted to digital data and received at the processor 20. The application (software package) embedded in the processor 20 is capable of analyzing these data and, upon detecting the existence of the predetermined condition as defined above (step 36), generates a signal actuating the transmitter 24 (step 38). The latter generates the radio warning signal which is duly received at the radio receiver 26 (step 40). The receiver 26, in response to this signal, actuates the indicator 11A (step 42) for generating an indication. alarm signal (step 44). As indicated above, the alarm signal should preferably be an audio signal much stronger than that of the transducer, as this alarm signal is aimed at waking the patient or attracting the attention of the authorized person.

Figure 7:
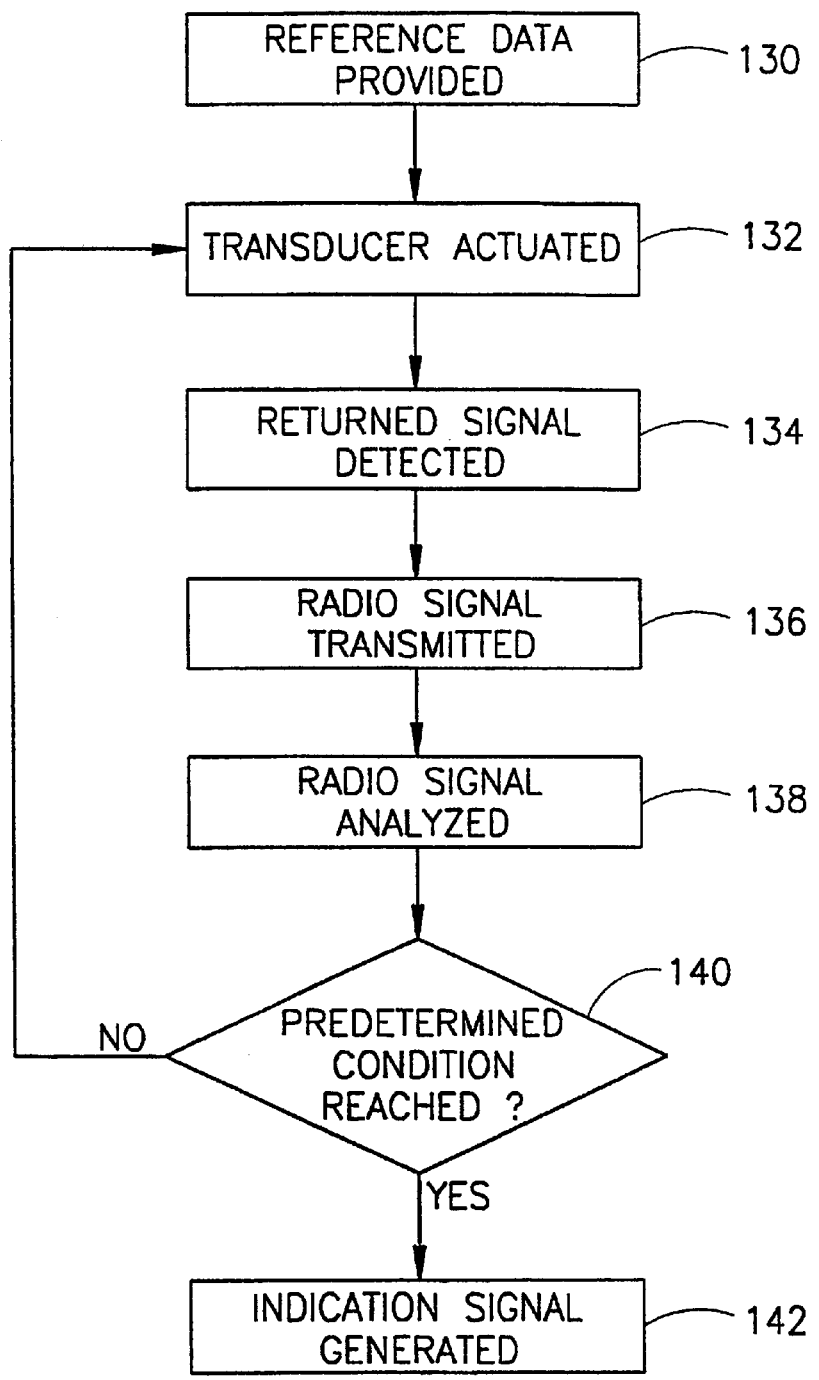
FIG. 7 is a flow diagram of the main operational steps of the device according to the embodiment of FIGS. 4a–4b.

The monitoring device, using the sensing unit 102 and the indication unit 104, operates in a manner illustrated in FIG. 7. The reference data is provided and stored in the memory of the processor 20 (step 130). To actuate the transducer 14 (step 132), the patient presses the switch 10 at the indication unit 104. The actuation of the switch 10 coupled to the processor 20 (FIG. 4b), results in that the processor 20 generates a corresponding signal which is transmitted through the D/A converter to the radio transceiver 29. The latter transmits a corresponding signal to the radio transceiver 28 of the sensing unit 102, which actuates the battery power source 16. The battery power source 16 and the transducer 14 operate together in the above-described manner, and reflected signals are periodically detected (step 134) and transmitted to the indication unit 104 through the radio transceiver 28 (step 136). The processor 20 analyzes the received signals (step 138), and, upon detecting the existence of the predetermined condition (step 140), generates the warning signal. This signal is received at the indicator 11A, that generates the indication alarm signal (step 142), which may be either audio or visual, as described above.

The advantages of the present invention are self-evident. The sensing unit utilizes either an audio or infrasound transducer, rather than an ultrasonic one, thereby operating with lower voltage and thus requiring a battery power source of smaller dimensions and lower cost. The low cost allows the sensing unit to be disposable, which, accordingly, eliminates the need for any additional attachment means by making the sensing unit as a patch. The acoustic insulation of the sensing unit enables the measuring audio or infrasound signals to be transmitted and received without affecting the patient, and only indication signals to attract his attention.

The indication signal so provided may be aimed at waking the patient himself, or attracting the attention of another authorized person, for example, the child's parent or physician, as the case may be.

The device according to the invention may also be used as an indicator of the condition of bladder urine distention level during a surgical intervention, thereby enabling an authorized person to make a decision as to whether to apply a urinal catheter to the patient or not. In this case, the sensing unit (assembly) should be attached to the patient's abdomen somewhat below the umbilicus and, then, moved slowly towards the pubic bone. During the movement of the device, the transducer generates and transmits audio (or infrasound) signals with the suitable time interval, e.g. 0.5–1 sec.

Those skilled in the art will readily appreciate that various modifications and changes may be applied to the preferred embodiments of the invention as hereinbefore described without departing from its scope as defined in and by the appended claims.

What is claimed is:

1. A device for monitoring a condition of a patient's bladder urine distention level, the device comprising:
   a sensing unit including an acoustic transducer formed by a transmitter operable to transmit acoustic signals of a high sound frequency to an urinary bladder of a patient through tissue, and at least one receiver for receiving reflections of the acoustic signals from the urinary bladder and generating data representative thereof;
   a processor responsive to said data for analyzing the data by comparing it to a predefined threshold value corresponding to a condition of a urinary bladder when urination is about to occur, and upon detecting existence of said condition generating a signal indicative thereof; and
   an indication unit responsive to said signal indicative of the existence of said condition for generating an indication signal to attract the attention of the patient or an authorized person,
   at least said sensing unit being accommodated in an acoustically insulating case, to be carried by a piece of patch attacheable to a location on the patient's abdomen.

2. The device according to claim 1, wherein said sensing unit comprises a power source coupled to the acoustic transducer for supplying thereto an alternating voltage of about 5V or less.

3. The device according to claim 1, wherein said transducer includes a piezoelectric element, and said high sound frequency is about 20 kHz.

4. The device according to claim 3, wherein said transducer is made of a ceramic material.

5. The device according to claim 1, wherein said transducer comprises at least two said receivers accommodated in a spaced-apart relationship in said case, said at least two receivers, when in an operative position of the device, being aligned along an axis of the bladder filling with urine, such that said at least two receivers detect the returned signals at two spaced-apart points, respectively, within said location on the patient's abdomen to which the sensing unit is attached.

6. The device according to claim 1, wherein said indication unit is wirelessly connected to said processor.

7. The device according to claim 1, wherein said indication unit is incorporated in a wrist-mounted device for attaching to the wrist of the patient or of the authorized person whose attention is to be attracted by the indication signal.

8. The device according to claim 1, wherein said processor is accommodated in said case.

9. The device according to claim 6, and also comprising a transmitter associated with said processor for transmitting said signal indicative of the existence of said condition, and a receiver associated with said indication unit for receiving said signal indicative of the existence of said condition.

10. The device according to claim 9, wherein said signal indicative of the existence of said condition is a radio signal.

11. The device according to claim 1, wherein said processor is accommodated in the indication unit.

12. The device according to claim 11, and also comprising an additional transmitter of the signal generated by the at least one receiver, said additional transmitter being accommodated in said case.

13. The device according to claim 1, and also comprising input means for preprogramming the processor with reference data representative of said condition for a specific patient.

14. The device according to claim 1, wherein said indication unit is accommodated in said acoustically insulating case.

15. The device according to claim 1, wherein said acoustically insulating case is replaceable from patient to patient.

16. A method for monitoring condition of a patient's bladder urine distention level with the monitoring device of claim 1, the method comprising the steps of:
   (a) attaching at least the transducer to a piece of patch and attaching said piece of patch to the patient's abdomen along a location thereon above a pubic bone;
   (b) actuating the transmitter for transmitting said acoustic signals to the urinary bladder, thereby causing the reflections of the acoustic signals from the urinary bladder to be received by the at least one receiver;
   (c) receiving and analyzing the data generated by the at least one receiver to detect existence of said condition;
   (d) upon detecting that said data is indicative of the existence of said condition, generating the indication signal to attract the attention of the patient or an authorized person.

17. The method according to claim 16, and also comprising the step of:
   converting said generated data into a wireless transmittable signal.

18. The method according to claim 17, and also comprising the step of:
   converting said signal indicative of the existence of said condition into a wireless transmittable signal.

19. A device for monitoring a condition of a patient's bladder urine distention level, the device comprising:
   a sensing unit including an acoustic transducer formed by a transmitter operable to transmit acoustic signals of a high sound frequency to a urinary bladder of a patient through tissue, at least one receiver for receiving reflections of said acoustic signals from the urinary bladder and generating data representative thereof, and a power source coupled to the acoustic transducer for supplying thereto an alternating voltage of about 5V or less;
   a processor responsive to said data for analyzing the data by comparing it to a predefined threshold value corresponding to a condition of a urinary bladder at which urination is about to occur, and capable of generating a signal indicative of the existence of said condition; and
   an indication unit responsive to said signal indicative of the existence of said condition for generating an indication signal to attract the attention of the patient or an authorized person, at least said sensing unit being accommodated in an acoustically insulating case, to be carried by a piece of patch attacheable to a location on the patient's abdomen.

20. A device for monitoring condition of a patient's bladder urine distention level, the device comprising:
   a sensing unit including an acoustic transducer formed by a transmitter operable to transmit acoustic signals of a high sound frequency to a urinary bladder of a patient through tissue, and at least two receivers associated with said transmitter and operating for receiving reflections of the acoustic signals from the urinary bladder and generating data representative thereof, said at least two receivers being accommodated in a spaced-apart relationship such that, when in an operative position of the device attached to a location on the patient's abdomen, they are aligned along an axis of the bladder filling with urine, said at least two receivers thereby detecting the returned signals in two spaced-apart points, respectively, within said location;

a processor responsive to said data for analyzing the data by comparing it to a predefined threshold value corresponding to a condition of a urinary bladder at which urination is about to occur, and capable of generating a signal indicative of the existence of said condition; and an indication unit responsive to said signal indicative of the existence of said condition for generating an indication signal to attract the attention of the patient or an authorized person;

at least said sensing unit being accommodated in an acoustically insulating case, to be carried by a piece of patch attacheable to the location on the patient's abdominal.

21. A device for monitoring a condition of a patient's bladder urine distention level, the device comprising:

a sensing unit including an acoustic transducer formed by a transmitter operable to transmit acoustic signals of a high sound frequency to a urinary bladder of a patient through tissue, at least one receiver for receiving reflections of said acoustic signals from the urinary bladder and generating data representative thereof;

a processor responsive to said data for analyzing the data by comparing it to a predefined threshold value corresponding to a condition of a urinary bladder at which urination is about to occur, and capable of generating a signal indicative of the existence of said condition;

an indication unit responsive to said signal indicative of the existence of said condition for generating an indication signal to attract the attention of the patient or an authorized person; and input means for preprogramming the processor with reference data representative of said condition for a specific patient;

at least said sensing unit being accommodated in an acoustically insulating case, to be carried by a piece of patch attacheable to a location on the patient's abdomen.

22. A device for monitoring a condition of a patient's bladder urine distention level, the device comprising:

a sensing unit including an acoustic transducer formed by a transmitter operable to transmit acoustic signals of a high sound frequency to a urinary bladder of a patient through tissue, at least one receiver for receiving reflections of said acoustic signals from the urinary bladder and generating data representative thereof;

a processor responsive to said data for analyzing the data by comparing it to a predefined threshold value corresponding to a condition of a urinary bladder at which urination is about to occur, and capable of generating a signal indicative of the existence of said condition; and an indication unit responsive to said signal indicative of the existence of said condition for generating an indication signal to attract the attention of the patient or an authorized person, at least said sensing unit being accommodated in an acoustically insulating case, to be carried by a piece of patch attacheable to a location on the patient's abdomen and to replaceable from patient to patient.

* * * * *